US010058287B2

(12) United States Patent
Meyer et al.

(10) Patent No.: US 10,058,287 B2
(45) Date of Patent: Aug. 28, 2018

(54) METHOD AND APPARATUS FOR ACQUIRING A MAGNETIC RESONANCE IMAGING DATASET

(71) Applicant: Siemens Aktiengesellschaft, Munich (DE)

(72) Inventors: Heiko Meyer, Uttenreuth (DE); Esther Raithel, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 241 days.

(21) Appl. No.: 14/994,580

(22) Filed: Jan. 13, 2016

(65) Prior Publication Data

US 2016/0199004 A1    Jul. 14, 2016

(30) Foreign Application Priority Data

Jan. 13, 2015    (DE) .......................... 10 2015 200 353

(51) Int. Cl.
*G06K 9/00* (2006.01)
*A61B 5/00* (2006.01)
*A61B 5/055* (2006.01)
*G06T 11/00* (2006.01)

(52) U.S. Cl.
CPC .............. *A61B 5/721* (2013.01); *A61B 5/055* (2013.01); *G06T 11/005* (2013.01); *G06T 11/008* (2013.01); *A61B 2560/0475* (2013.01); *G06T 2210/41* (2013.01)

(58) Field of Classification Search
CPC . A61B 5/721; A61B 5/055; A61B 2560/0475; G06T 11/008; G06T 11/005; G06T 2210/41

USPC .................................................. 382/128–132
See application file for complete search history.

(56) References Cited

U.S. PATENT DOCUMENTS

| 6,614,225 | B1   | 9/2003 | Feinberg |             |
|-----------|------|--------|----------|-------------|
| 7,545,967 | B1 * | 6/2009 | Prince   | G06T 5/50   |
|           |      |        |          | 128/920     |
| 2007/0201613 | A1 * | 8/2007 | Lu    | A61N 5/1049 |
|           |      |        |          | 378/65      |
| 2010/0160989 | A1 * | 6/2010 | Legay | A61N 1/37   |
|           |      |        |          | 607/4       |

(Continued)

OTHER PUBLICATIONS

Moghari et al.: "Compressed-Sensing Motion Compensation (CosMo). A Joint Prospective-Retrospective Respiratory Navigator for Coronary MRI", Magnetic Resonance in Medicine, vol. 66, pp. 1674-1681 (2011).

(Continued)

*Primary Examiner* — Andrew Moyer
(74) *Attorney, Agent, or Firm* — Schiff Hardin LLP

(57) ABSTRACT

In a method and apparatus for acquiring a magnetic resonance imaging dataset of an area to be examined of a patient by magnetic resonance data are acquired over a prespecified acquisition period which has been fixed for the acquisition process. This acquisition period is divided into a number of sub-periods. For each sub-dataset of the magnetic resonance data acquired by undersampling in a sub-period, at least one motion value describing the motion status of the area to be examined is determined, and the data subsets to be used for the reconstruction of the magnetic resonance imaging dataset are selected in dependence on the motion values in order to minimize motion artifacts.

29 Claims, 3 Drawing Sheets

(56) References Cited

U.S. PATENT DOCUMENTS

| | | | | |
|---|---|---|---|---|
| 2010/0222666 A1* | 9/2010 | Foo | ........................ | A61B 5/055 600/413 |
| 2011/0230755 A1* | 9/2011 | MacFarlane | ........... | A61B 5/055 600/414 |
| 2012/0283549 A1* | 11/2012 | Miyazaki | ........... | G01R 33/5673 600/413 |
| 2014/0035582 A1* | 2/2014 | Boernert | ............ | G01R 33/5611 324/312 |
| 2014/0084924 A1 | 3/2014 | Grodzki | | |
| 2014/0125335 A1 | 5/2014 | Li et al. | | |

OTHER PUBLICATIONS

Kolbitsch. et al.: "A 3D MR-acquisition scheme for non-rigid bulk motion correction in simultaneous PET-MR."; Medical Physics, vol. 41; No. 8; pp. 082304-1-082304-14; (2004).

Kober et al.: "Head Motion Detection Using FID Navigators", in: Magnetic Resonance in Medicine; vol. 66; No. 1; pp. 135-143; (2011).

Hardy. et al.: "Coronary MR Angiography: Respiratory Motion Correction with BACSPIN"; Journal of Magnetic Resonance Imaging ; vol. 17; pp. 170-176 (2003).

Larkman et al., "Use of Multicoil Arrays for Separation of Signal from Multiple Slices Simultaneously Excited," Journal of Magnetic Resonance Imaging, vol. 13, pp. 313-317 (2001).

Setsompop et al., "Blipped-Controlled Aliasing in Parallel Imaging for Simultaneous Multislice Echo Planar Imaging With Reduced g-Factor Penalty," Magnetic Resonance in Medicine, vol. 67, pp. 1210-1224 (2012).

Griswold et al, "Generalized Autocalibrating Partially Parallel Acquisitions (GRAPPA)," Magnetic Resonance in Medicine, vol. 47, pp. 1202-1210 (2002).

* cited by examiner

METHOD AND APPARATUS FOR ACQUIRING A MAGNETIC RESONANCE IMAGING DATASET

BACKGROUND OF THE INVENTION

Field of the Invention

The invention concerns a method for acquiring a magnetic resonance imaging dataset of an area to be examined of a patient by operation of a magnetic resonance apparatus, as well as a magnetic resonance apparatus for implementing such a method.

Description of the Prior Art

Magnetic resonance imaging has become established for the examination of patients in medical practice. One frequently discussed problem is the measuring time required for the acquisition of magnetic resonance data. Depending upon the resolution, the acquisition of a magnetic resonance imaging dataset, in particular an at least three-dimensional magnetic resonance dataset, can necessitate a measuring time of from a few milliseconds to several minutes. The higher the desired resolution, the longer the estimated acquisition period. High resolution is necessary in the case of orthopedic diagnoses, for example, for the evaluation of cartilage damage, tendon injuries or ligament injuries. In such cases, the contrast required can result in measuring times ranging from 3 to 10 minutes.

Various possibilities are known for reducing the acquisition period, by the term "accelerated imaging". Examples of this include parallel imaging, see for example the article by M Griswold et al, "Generalized autocalibrating partially parallel acquisitions (GRAPPA)", Magn. Reson. Med. 47 (2002), pages 1202-1210, simultaneous multi-slice imaging, see for example in this regard the article by E. J. Larkman et al., JMRI 13 (2001), pages 313-317, or the article by K. Setsompop et al., MRM 67 (2011), pages 1210-1224, and simultaneous imaging refocusing, see for example in this regard U.S. Pat. No. 6,614,225 B1. However, with all these methods, the result of the measurement is only visible following complete data acquisition and it is only at this time that it is possible to evaluate whether the measurement has to be repeated, for example due to a motion of the patient. This extends the duration of the examination.

Since, it is not known prior to a measurement whether the image quality is excessively impaired by the patient motion, it is not possible to predict the overall duration of the examination and so patients' appointments have to be planned correspondingly generously. Without generous planning of this kind, delays in the time schedule may occur. In the first instance, fewer patients can be examined and additional costs are incurred since the magnetic resonance system is not permanently used at full capacity. In the second case, patients are subjected to waiting times and this has a negative impact on satisfaction with the medical service.

A further problem relating to motions that occur during the acquisition of magnetic resonance data is that even the operator present at the magnetic resonance mechanism during the examination is unable to determine in all measurements whether the patient moves. Only specific magnetic resonance sequences, for example for neurofunctional imaging, measure motion during the acquisition of magnetic resonance data.

To date, on the occurrence of a motion in the area of the patient to be examined, it has only been decided at the end of the measurement, that is when the magnetic resonance imaging dataset is available, whether a new measurement, therefore a new acquisition of magnetic resonance data from the patient, is necessary.

In order to achieve improvements in the light of this problem, US 2014/0125335 A1 suggested a method with which the occurrence of motions is monitored during the measurement in order to stop the acquisition of data if necessary. Therefore, this publication relates to a method for magnetic resonance imaging with which the acquisition process is divided into two parts, namely an essential component ("basic acquisition") and an additional component ("complementary acquisition") by means of which an improvement in image quality can be achieved until a motion occurs. The essential part of the acquisition is performed at the start and finally includes a sub-sampled basic dataset from which reconstruction would already be possible in principle. The further acquisition process of indeterminate length supplements this data. In this case, only one maximum measuring time is disclosed. If a motion occurs in the essential part of this measurement, the entire measurement has to be repeated. Therefore, in this case, the motion monitoring relates to the motion status in the area to be examined at the start of the acquisition process.

However, the method described in US 2014/0125335 A1, facilitates neither improved planning, since it can still be the case that measurements have to be completely repeated and the acquisition period varied, nor reliably high image quality, since it is possible that the acquisition is aborted very early on in the complementary component of the measurement.

SUMMARY OF THE INVENTION

An object of the invention is to provide an improved method in comparison to the above, which, together with good planning, provides the best possible image quality of the magnetic resonance imaging dataset.

This object is achieved by a method in accordance with the invention wherein magnetic resonance data are acquired during a prespecified acquisition period, which has been fixed for the acquisition process, and wherein the acquisition period is divided into multiple sub-periods, that are preferably equally long, with respective data subsets of the magnetic resonance data being individually acquired by undersampling in each sub-period. At least one motion value, that describes the motion status of the area to be examined, is determined for each data subset, and the data subsets to be used for the reconstruction of the magnetic resonance imaging dataset are selected in dependence on these motion values, in order to minimize motion artifacts.

As is known to those of ordinary skill in the field of magnetic resonance imaging, the raw magnetic resonance data that are acquired from a patient are entered into an electronic memory that represents k-space, as k-space data, and an image is then reconstructed in a known manner from the k-space data. The electronic memory that represents k-space has a number of data entry points therein that are each potentially available for making a data entry thereat. The k-space points are determined by whatever coordinate system is used to organize k-space in the memory. Sampling or scanning of k-space means that the raw magnetic resonance data are entered at respective points in k-space. An undersampling of k-space means that there will be some data points in k-space, at which a data entry does not take place, and thus there will be a certain number of empty (unfilled) data entry points in k-space.

The invention can be applied with all types of magnetic resonance datasets, but preferably to at least three-dimensional magnetic resonance datasets. Examples include multi-slice imaging, with which a number of two-dimensional slices are acquired, three-dimensional static imaging, and three-dimensional dynamic imaging (with 3+1 (time) dimensions). Higher-dimensional magnetic resonance image data are also provided with other methods, for example multi-contrast-imaging. A series with two-dimensional images, the magnetic resonance data (raw data) of which are acquired interleaved with TSE sequences, provides significant sensitivity to motions.

Therefore, as in the case of the afore-mentioned prior art, the approach of undersampling is selected with the undersampling factor being reduced by repeated measurements, but conventionally this approach has not been based on a reference motion status. Instead in accordance with the invention, a fixed prespecified measuring time, namely the acquisition period, is used, during which magnetic resonance data are acquired continuously. In accordance with the invention, with permanent motion tracking, which enables sub-periods in which data subsets of the magnetic resonance data are acquired to be individually assigned at least one motion value, describing the motion status of the area to be examined. The respective motion values of the data subsets now enable an evaluation to be made after the measurement of the magnetic resonance data. The evaluation determines for which motion status or for which motion status range, the highest quality magnetic resonance imaging dataset can be reconstructed so that only the data subsets among the magnetic resonance data that satisfy the evaluation criterion are used in the image reconstruction. Usually, at least one selection criterion for the data subsets will relate to the motion status or motion status range from which the majority of magnetic resonance data originates, so that the lowest undersampling factor is obtained. Therefore, in summary, in accordance with the invention, the duration of the acquisition period for the acquisition process is kept constant and the best possible image quality is ensured in that magnetic resonance image datasets are reconstructed from the magnetic resonance data acquired with respect to a specific motion status without movement, and possibly also from magnetic resonance data that can be successfully subjected to motion correction by suitable iterative, non-linear or linear image reconstruction methods. In this case, the acquisition process can be planned such that the time point of a patient motion during the acquisition process is irrelevant.

Preferably, the image reconstruction is three-dimensional. It is important that the acquisition of the magnetic resonance data be performed by undersampling, such as in a stochastic, pseudo-randomized or specially ordered form, so that a magnetic resonance imaging dataset, such as a 3D image data set, can still be reconstructed even if not all the magnetic resonance data are available. Specific embodiments for this will be discussed in more detail below. Reconstruction techniques are known in the prior art that enable as uniform as possible coverage of k-space corresponding to the area to be examined, so that the omission of a part of the magnetic resonance data in some data subsets has hardly any influence on the basic high-quality reconstruction. In another embodiment, for several or even all data subsets, a specific region around the k-space center is filled with data in order to ensure as far as possible that sufficient coverage is available therein.

Contrary to known imaging methods, the measuring time defined by the prespecified acquisition period is known in advance and the reconstruction is performed with the best possible image quality, whereas, according to the prior art, measurements may have to be repeated, or it is unclear at the start how long the measuring time will be. The subsets may contain only one data point, and are evaluated with reference to motion monitoring. Local criteria can be used for this purpose, for example an evaluation of the degree of the motion at a single time point, but preferably also global selection criteria are taken into account, which, for example, determine which magnetic resonance data are to be used in which way, in order to minimize motion artifacts and maximize the signal-to-noise ratio.

In an embodiment of the invention, the motion value, or at least one of the motion values, is determined from the magnetic resonance data of the sub-dataset itself, such as by acquiring a navigator in the magnetic resonance data of the sub-dataset in the spatial domain and/or by determining a quality measure for the sub-dataset. It is thus possible for magnetic resonance data of the sub-dataset itself to be evaluated in order to determine at least one motion value. To this end, particularly when the sub-dataset contains data from the k-space center, it is possible for a one-dimensional navigator to be reconstructed from the magnetic resonance data. The motion value can be determined, for example, as the position of an edge of the navigator. Obviously, the choice of the position of the navigator can be based on background knowledge on the area to be examined, which can be derived, for example, from a localizer scan or the like. It is also conceivable for a quality measure to be determined for the sub-dataset that indicates how noisy the magnetic resonance data of the sub-dataset are.

Moreover, the motion value or at least one of multiple motion values is determined by a measurement separate from the acquisition of the magnetic resonance data. There are several procedures conceivable for this purpose. For example, a navigator measurement can be performed with the magnetic resonance scanner, for the measurement of the motion value. Navigator measurements of this kind are known and entail one-dimensional measurements, which are able to track the position of an edge, for example during diaphragmatic breathing. The at least one navigator measurement per sub-dataset can be performed before or after the measurement of the corresponding sub-dataset, but other magnetic resonance sequences are also conceivable with which the navigator measurement can be ultimately embedded in the course of the actual acquisition of the magnetic resonance data. A further possibility for a measurement that can be performed outside the acquisition of the magnetic resonance data is a further measuring device in addition to the magnetic resonance scanner. Such devices for motion tracking in magnetic resonance scanner are known and can be used for the purposes of the present invention. For example, camera tracking, a marker arranged on the patient, and/or a breathing belt and/or reference probes that measure the magnetic field such as a field camera, can be used as further measuring means.

The present invention uses procedures that are in principle known in order to be able to acquire magnetic resonance data by undersampling in k-space but in a different way that enables a complete, higher-quality reconstruction to be performed. The distribution of the points sub-sampled in k-space should be selected across all data subsets such that reconstruction from only some of the data subsets is enabled. In this case, two basic approaches are conceivable. One is coherent undersampling, with which a regular sampling pattern, for example every n-th point in k-space. Another is incoherent undersampling, such as stochastic and/or pseudo-randomized sampling. Therefore, with coherent acquisition of magnetic resonance data, there are regular intervals between the individual data points in k-space. Therefore, the entire acquisition process (scan) is divided into several sub-acquisition processes (single scans) all of which have a relatively high undersampling factor in one or more phase-encoding directions, wherein the sampling schemes of the data subsets are appropriately offset with respect to one another so that they can be assembled to form a combination dataset with a lower undersampling factor. While aliasing artifacts are more clearly evident with coherent undersampling and can generally be dealt with by suitable reconstruction algorithms, with incoherent undersampling, the aliasing should be regarded as being similar to noise.

Therefore, in an embodiment of the invention, sampling of k-space assigned to the area to be examined in the sub-periods takes place stochastically or pseudo-randomly. In addition to known stochastic sampling methods, which are aimed at a uniform distribution of the sampled points in k-space at least outside the k-space center, a pseudo-randomized approach is also conceivable, for example a special specification within which the randomly selected sampling is performed. Alternatively, regular patterns for the sampling of k-space assigned to the area to be examined are conceivable, for example the regular omission of points in k-space in one or more phase-encoding directions. In principle, for the purposes of the present invention, both radial sampling schemes and Cartesian sampling schemes are conceivable, in particular also used in combination. Expediently, the reconstruction of the magnetic resonance imaging dataset from the selected magnetic resonance data with incoherent sampling can be performed in accordance with an iterative reconstruction method or, in the case of coherent sampling, in accordance with a linear reconstruction method, in particular a GRAPPA method or a SENSE method. Other known techniques with respect to sub-sampled magnetic resonance data can also be used for the reconstruction of the preferably three-dimensional magnetic resonance imaging dataset. Generally, different techniques such as "compressed sensing", parallel imaging and the like such as those already mentioned above can be used for the purposes of the present invention.

In another embodiment of the invention, the data subsets are sorted into at least two motion status classes with reference to the motion value. Therefore, the measured magnetic resonance data, sorted in data subsets to which motion values are assigned, can be classified according to different motion phases or generally different motion statuses. Preferably, at least those data subsets of the motion status class which contain the majority of the magnetic resonance data and/or meet a quality criterion for the motion value describing the suitability for the reconstruction are selected for the reconstruction of the magnetic resonance imaging dataset. Therefore, the motion status in which the majority of magnetic resonance data is present or the magnetic resonance data of which is most suitable for reconstruction is used as the basis for the reconstruction of the, in particular three-dimensional, magnetic resonance imaging dataset.

In this case, it is obviously not necessary to discard all other motion status classes outside the selected motion status class. For example, an advantageous variant of the invention envisages that, in addition to the magnetic resonance data from the selected motion status class, the magnetic resonance data from at least one further motion status class satisfying a deviation criterion for the motion values with respect to the motion values of the data subsets of the selected motion status classes is also taken into account. This means it is also possible to use magnetic resonance data from motion status classes with a motion status or motion status range close enough to the motion status or motion status range of the selected motion status class. In this context, it is particularly advantageous for the magnetic resonance data of different motion status classes to be weighted, in particular with a weighting selected in dependence on a deviation of the motion values of its motion status class from those of the selected motion status class. Therefore, different motion statuses can be included in the reconstruction with different degrees of weighting, wherein the weighting is performed according to different criteria, but preferably based on the deviation of the motion status from the motion status of the selected motion status class. It is possible for different mathematical functions to be used in order to determine the weighting factors, for example in the sense of linear and/or exponential attenuation. A weighted consideration of further magnetic resonance data of this kind can, incidentally, be achieved particularly simply when iterative reconstruction of the magnetic resonance imaging dataset is performed. Overall, taking into consideration further magnetic resonance data from other motion status classes enables the signal-to-noise ratio to be improved since more magnetic resonance data is used for the reconstruction.

It should be noted that motion status classes are usually defined over intervals of the at least one motion value assigned to each of the data subsets. In this case, it is obviously also possible for motion status classes to be defined dynamically, for example by determining the entire interval within which the motion values lie and which can then be subdivided appropriately. It is also possible for a histogram analysis to be performed also with respect to the selection of at least one motion status class, which indicates, for example how many events occur in which intervals of the motion values and the like.

A further embodiment of the present invention takes into account further magnetic resonance classes in addition to the magnetic resonance data from the selected motion status class. In this embodiment, in addition to the magnetic resonance data from the selected motion status class, magnetic resonance data from at least one further status class, which describe the possibility of correcting the differences that occur due to the motion following a corresponding correction, are also taken into account. Thus, it is possible to monitor whether motion statuses exist for which the motion can be corrected with respect to the motion status or motion status range of the selected motion status class. Thus, the motion status best suited for the reconstruction can be expanded by the low-motion statuses up to the motion statuses for which, for example, successful registration can be performed. The correctability criterion can thus determine a measure for a successful registration of an intermediate image dataset determined from the magnetic resonance data from the selected motion status class with an intermediate image dataset determined from the magnetic resonance data from the motion status class to be determined, in particular with reference to a mutual information measure and compares it with a threshold value. Mutual information measurements actually represent variables indicating whether successful registration is conceivable and therefore magnetic resonance data for a motion status can be retropolated to the motion status of the selected motion status class.

In another embodiment, during the performance of motion correction, the motion values and/or further motion data determined during the determination of the motion values are evaluated for the determination of at least one motion parameter modeling the motion and/or for the restriction of at least one value range during a registration. Such motion data and/or the motion values themselves can also be included in the correctability criterion, which can also take account of the available information. The concept behind this variant is that the data from the monitoring of the patient motion can also be used for the motion correction. At the same time, it is possible for the actual motion in the area to be examined to be estimated, and it is possible for the value range of the registration parameters to be restricted during registration.

Embodiments in which motion correctability is checked, and motion-corrected magnetic resonance data of other motion status classes outside the selected motion status class can be taken into account, have been found to be particularly advantageous when a number of motion status classes each with a relatively large amount of magnetic resonance data, i.e. data subsets, are present. This is the case, for example, when a single stronger motion divides the acquisition period into two components that are motion-free or at least have very little motion. This can occur if the patient falls asleep during the acquisition process and, for example, tilts his or her head toward the side. With conventional methods, it would then be necessary to repeat the complete measurement. In the embodiment of the inventive method in which checks for motion corrections are also performed, the method according to the invention advantageously still enables the inclusion of virtually all magnetic resonance data in the reconstruction of the magnetic resonance imaging dataset. In the case of at least two larger "blocks" of magnetic resonance data, this is due to the fact that for each of these blocks, intermediate image datasets can be generated in the spatial domain, which are enough to enable a sufficient degree of registration for the motion-corrected phases of a motion status to be retropolated to the motion status, or to a representative motion status of the motion status range of the selected motion status class.

In a further embodiment, for at least one reserved sub-period, at the end of the acquisition period, the measurement of a sub-dataset already measured in a previous sub-period is repeated, wherein the sub-dataset to be repeated is selected dynamically with reference to an evaluation of the motion values of all datasets set up to this sub-period. When a sub-dataset is acquired again, the previous magnetic resonance data of the sub-dataset can be discarded. Therefore, in this variant of the method according to the invention, at the end of the acquisition period, a part of the entire measuring time, that is of the prespecified acquisition period, is reserved in order to acquire a part of the preceding data points. Although these additional sub-acquisition processes for data subsets can be defined in accordance with a fixed prespecified scheme, it is preferable make a determination dynamically as to which of the previously acquired magnetic resonance data and the motion values which magnetic resonance data should be acquired again. For example, the part or parts of the magnetic resonance data most disrupted by motion in the area to be examined can be identified by the motion monitoring, and then discarded. For example, a histogram analysis can be performed during division into motion status classes. This is particularly advantageous when it is expected that motions will take place for a short time with the patient then returning approximately to his or her original position. Typical examples of short-term motions of this kind are twitching, coughing, swallowing motions, blinking and the like.

It is also possible for the number of reserved sub-periods to be selected in dependence on patient information describing the motions to be expected. If it is known in advance whether the particular patient to be examined is expected to produce more or less motion, the number of reserved sub-periods can be adapted accordingly. It is also conceivable for patient information used that was determined from at least one preceding measurement of the patient in the magnetic resonance scanner. Patient behavioral information can additionally or alternatively be used, that can be entered by a technician/operator. In addition to information about the status of the patient provided by an operator, it is also possible for this information to be determined automatically from previous measurements, for example localizer scans or preceding magnetic resonance measurements in the current examination. A variant is also possible wherein the number of reserved sub-periods is only defined dynamically during the acquisition process. For example following a specified number of sub-periods, the motion values acquired to date are evaluated for the determination of the patient information, which then indicates how high the level of the patient's motion should be assessed, in comparison with such empirically determined reference values.

As explained above, it is expedient for the data subsets to be mutually supplementary with respect to the sampled data points in k-space so that, in all data subsets, or at least all data subsets to be acquired before a reserved sub-period, at least some different components of k-space assigned to the area to be examined are sampled. For example, at least two, in particular all, sub-periods for a predetermined region around the k-space center of k-space corresponding to the area to be examined, are sampled completely. This ensures, when the k-space center regions filled in all data subsets, magnetic resonance data from the k-space center are available for each motion status in question. It is also expedient if, taking together all and/or one predetermined component of the data subsets, a predetermined undersampling factor is obtained. If it is empirically known that, due to motions, usually 80% of the acquired magnetic resonance data can be used, it is expedient to arrange different sub-sampled components of k-space for the different sub-periods as equally distributed as possible. When using a component of magnetic resonance data of this kind, a specific, desired undersampling factor, for example the undersampling factor 2, is obtained. In this way, ultimately an acquisition concept is created that ensures uniform sampling of k-space and ensures a certain level of image quality.

The concept of the invention can also be developed such that the magnetic resonance imaging dataset is acquired at the end of an examination including a number of partial examinations with the magnetic resonance scanner, wherein the fixed acquisition period for the acquisition process is specified as a predetermined, defined examination duration minus the durations of the preceding partial examinations. In practice, it is frequently the case that the three-dimensional measurement from which the three-dimensional magnetic resonance imaging dataset is to be produced is performed at the end of a total examination process on the patient. It is now possible, such as within the context of the planning of the usage of the magnetic resonance scanner over a specific period, to define an examination duration for the examination in advance. Before or during a part of the acquisition process for the dimensional, magnetic resonance imaging dataset, the time available for the acquisition thereof can be dynamically calculated with reference to the components of the examination duration already executed for the examinations. If the preceding examinations can be performed particularly quickly, before the start of the acquisition process, the acquisition period can be specified as longer. If more time was required for the preceding examinations, a correspondingly shorter time is available for the fixed acquisition period for the acquisition of the magnetic resonance data.

In a further, preferred embodiment of the invention, data subsets are selected as early as during the acquisition period and a preceding-image dataset is reconstructed on the basis thereof. When the preceding-image dataset satisfies a quality criterion describing a minimum image quality requirement, the acquisition process is aborted before the expiration of the acquisition period, and the most recently determined preceding-image dataset is used as a magnetic resonance imaging dataset. This embodiment is based on the concept that, during the arrangement and division of the acquisition period into sub-periods with respect to the magnetic resonance data to be acquired in the sub-periods, a certain buffer is to be created which, even upon the occurrence of magnetic resonance data that are non-correctable and/or cannot be taken into consideration with weighting, nevertheless enables the reconstruction of a sufficiently high-quality magnetic resonance imaging dataset. However, if it is the case that no motions occur over a lengthy period that would result in magnetic resonance data being discarded, and so a magnetic resonance imaging dataset of the desired quality can be reconstructed before the expiration of the acquisition period, it is no longer necessary also to acquire the remaining magnetic resonance data, and the acquisition can be aborted. Therefore, to this end, in real time, at least a portion of a preceding-image dataset is reconstructed from selected data subsets, or possibly further, data subsets that are weighted and/or taken into account subject to motion correction, and is checked with respect to the requisite image quality. If the image quality is sufficient, i.e. the quality criterion is satisfied, the acquisition can be aborted before the expiration of the acquisition period. In this case, it is particularly expedient for the evaluation of the quality criterion to be performed for a predetermined, two-dimensional slice in the area to be examined, since it is then easier to achieve real-time execution, thus enabling savings of calculation resources.

In another embodiment of the invention, during the acquisition process, if motion values are determined that satisfy an output criterion indicating excessive motion, that a predictive calculation shows will likely result in a failure to satisfy a quality target for the magnetic resonance imaging dataset, alerting information is emitted to notify the patient and/or an operator of the excessive motion. Therefore, if it is already evident from the motion values during the acquisition process that there is a risk that it will not be possible for the desired quality target to be achieved, the patient can be requested by the emission of the alerting information to reduce the number or extent of motions, if possible. In this way, it can be dynamically monitored during the acquisition process as to whether the patient is capable of sufficient cooperation for achieving an image of the necessary quality. Alerting information of this kind can also be provided to the operators, who can then calm the patient and encourage him or her to cooperate more fully. Hence, feedback of the motion monitoring is generated that can be used directly during the acquisition process.

It is also noted that, with the practical use of the method according to the invention, the acquisition periods usually will be within the range of minutes, for example in the range of 1 to 10 minutes. Correspondingly, sub-periods will tend to be in the range of seconds, for example 1 to 10 seconds.

In addition to the method, the invention also concerns a magnetic resonance apparatus having a control computer that operates a scanner of the apparatus, with the control computer being configured to do so according to the method of the invention. All explanations with respect to the method according to the invention apply analogously to the magnetic resonance apparatus according to the invention, with which, therefore, it is able possible to obtain the aforementioned advantages. In particular, therefore, the control computer has an acquisition stage or module or processor that is able to control components of the magnetic resonance scanner for acquiring magnetic resonance data. Optionally, in a suitable embodiment, the control computer can operate the scanner to acquire a navigator (navigator data). In addition, the control computer has a motion monitoring stage or module or processor that to determine the motion values for the different sub-periods and to assign the corresponding data subsets. In a reconstruction computer, the data subsets or motion status classes to be used for the reconstruction of the, in particular three-dimensional, image dataset are selected with reference to the motion values and the reconstruction is carried out. Further units can implement further steps of the method according to the invention.

DESCRIPTION OF THE PREFERRED EMBODIMENTS

Figure 1:
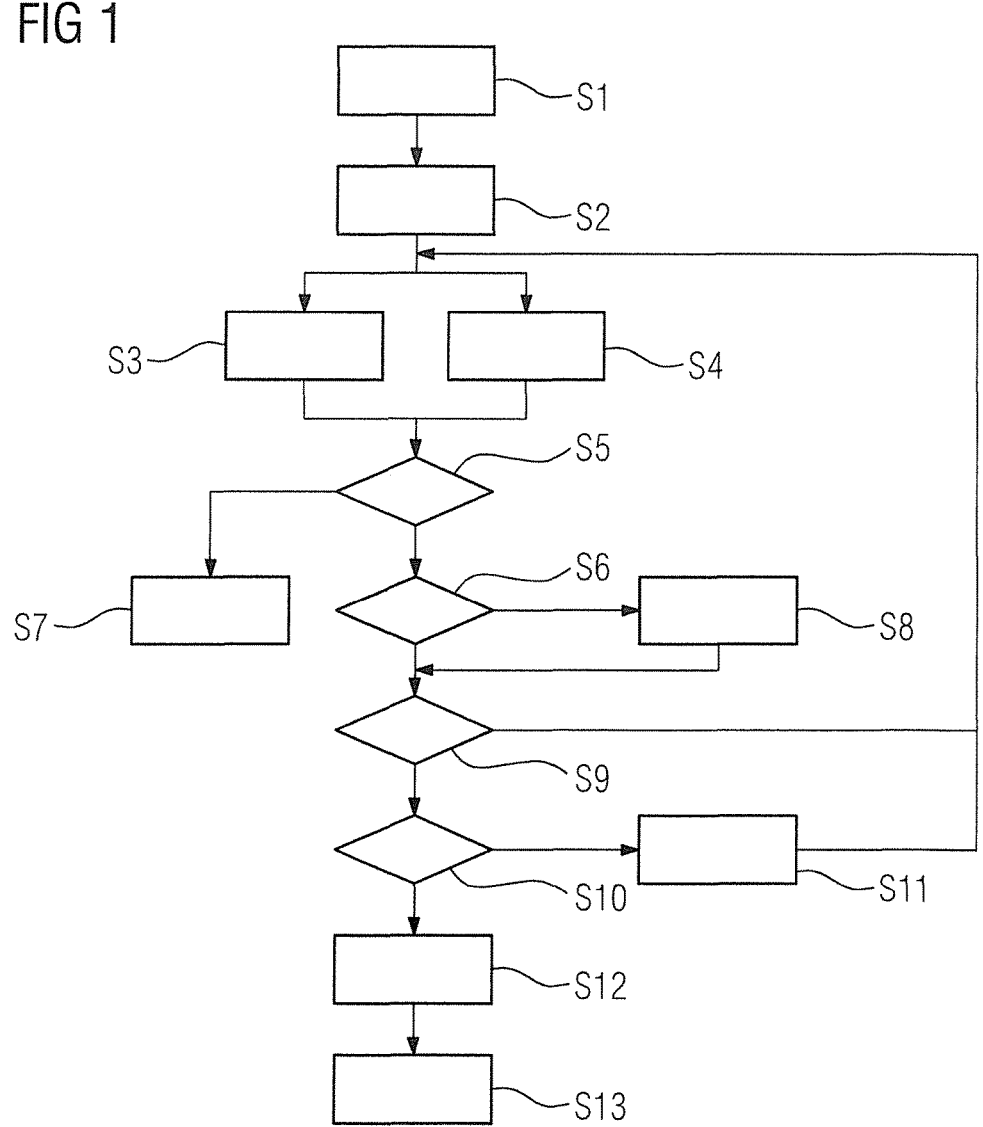
FIG. 1 is a flowchart of an exemplary embodiment of the method according to the invention.

The following now describes exemplary embodiments of the method according to the invention. The method entails the acquisition of a three-dimensional magnetic resonance imaging dataset of an area to be examined of a patient that could possibly be subjected to motion, but the method can also be used with other dimensionalities. In this case, the acquisition process for the corresponding magnetic resonance data on which the reconstruction of the three-dimensional magnetic resonance imaging dataset should be at least partially based is carried out at the end of an examination. Therefore, in order to specify the fixed acquisition period for the acquisition process, in Step S1 the durations of the preceding partial examinations of the examination are added up and subtracted from the predetermined, defined examination duration, which is also used as the basis for planning the usage of the magnetic resonance mechanism. It is also possible for a maximum length of the acquisition period to be defined that is not exceeded, so that the overall examination duration then turns out to be shorter that was assumed, but this is not disadvantageous.

In a Step S2, the fixed acquisition period prespecified in this way is now divided into sub-periods, in each of which magnetic resonance data are to be acquired. Therefore, the entire acquisition process is divided into partial acquisitions. At the same time, each sub-dataset is undersampled, but within each sub-dataset, a complete sampling of a region around the center of k-space corresponding to the area to be examined is completely sampled in order to have data relating to this in each case. Other examples are a more sparse, but nevertheless multiple, sampling of the region around the k-space center. In this way, it is ensured that data from the center of the k-space are at least available for the subsequently relevant motion statuses. In this case, the undersampling for the data subsets is selected in each case such that the individual data subsets are supplemented, therefore the undersampling factor falls with the combination of several data subsets. Moreover, when planning the acquisitions in the sub-periods, it should be noted that, with different combinations of data subsets, as uniform as possible distributed sampling of the k-space corresponding to the area to be examined is nevertheless obtained. It is preferable for stochastic or pseudo-randomized undersampling to be performed. It is possible for diverse types of undersampling to be used for which it is known that corresponding reconstruction method for three-dimensional magnetic resonance image datasets can be used correspondingly. Corresponding procedures permitting sampling patterns that are distributed as uniformly as possible even with different combinations of data subsets have already been suggested; for example, it is possible to use concepts with which, during radial sampling, successive spokes to be sampled radially in the k-space always have the spacing of a golden angle and the like.

In the present exemplary embodiment, an operator has already entered patient information that indicates the expected degree of the motions of the patient, in particular in the area to be examined, such as, for example, whether the patient is rather calm or rather anxious, suffers from claustrophobia and the like. Motion information of this kind can also be already derived from previous acquisitions with the magnetic resonance mechanism, for example from the results of the preceding partial examinations and/or localizers acquired. This patient information is used to define a number of reserved sub-periods at the end of the acquisition period which are used for the repetition of the acquisition of data subsets classified as unsuitable for the reconstruction. This will be dealt with in more detail below.

Now, in a Step S3, the acquisition of the magnetic resonance data of the data subsets in the corresponding sub-periods commences, wherein parallel to each sub-dataset, at least one motion value is determined describing the motion status of the area to be examined during the acquisition of the sub-dataset. While this can, in principle, already be derived from the magnetic resonance data of the sub-dataset itself, for example by the suitable placing of a navigator, in particular when the k-space center was sampled at the same time, additional navigator measurements with the magnetic resonance mechanism such as are known in principle in the prior art are also possible. It is also possible for additional measuring means to be used, for example breathing belts, optical sensors tracking markers, in particular cameras, field-camera-based tracking possibilities for motion and the like. At the same time, obviously cumulative use of sources for the motion status of the patient, in particular the area to be examined, are conceivable, wherein then correspondingly more motion values can be used and/or a motion value can be assembled as a partial combination of motion data.

Following the acquisition of each sub-dataset or even during the acquisition of the next sub-dataset, the optional Steps S5 and S6 are performed in each case, wherein optionally it is also possible for a threshold in the form of a minimum number of data subsets, which have already been acquired to be provided before the checks in the optional Steps S5 and S6 are performed.

Finally, in Step S5, a preceding-image dataset is reconstructed from selected data subsets, as will be described in more detail, below and a check is performed as to whether this preceding-image dataset already satisfies a quality criterion describing a minimum image quality requirement. At the same time, in order to enable real-time implementation of the optional Step S5, the quality criterion is preferably evaluated in a two-dimensional slice image. If the quality target has already been achieved before the end of the acquisition period, according to Step S7, the acquisition process can be aborted at this stage, wherein the corresponding preceding-image dataset can then be used as a three-dimensional magnetic resonance imaging dataset.

In the optional Step S6, the motion values acquired so far are evaluated with reference to an output criterion as to whether there is a risk that the quality target for the three-dimensional magnetic resonance imaging dataset will not be satisfied if the motion activity of the patient is correspondingly continued. If this is the case, in a Step S8, alerting information is output to the patient and an operator, if present, indicating that the motion activity should be reduced.

In a Step S9, it is asked whether a reserved sub-period was achieved at the end of the acquisition period. If not, the next sub-dataset is acquired for a non-reserved sub-period. If, however, the end of the acquisition period is not achieved, which is checked in Step S10, and if a sub-dataset is to be acquired in a reserved sub-period, it is decided in Step S11 by an evaluation of the motion values available so far which sub-dataset is to be acquired again in the reserved sub-period.

This is explained in more detail with reference to FIG. 2. This is a schematic diagram of the fixed acquisition period 1 for the acquisition process, which is divided into corresponding sub-periods 2, 3. Three sub-periods lying at the end of the acquisition period 1 form the reserved sub-periods 3. Therefore, as indicated in the lower region of FIG. 2, at time point 4, for example, a specific number n of data subsets 5 with assigned motion values 6 are available. An analysis of the motion values 6, in particular a histogram analysis, as will be performed later also with respect to the reconstruction of the three-dimensional magnetic resonance imaging dataset, enables a decision to be made as to which magnetic resonance data of which sub-dataset is probably particularly unsuitable or most unsuitable to be used for the reconstruction of the three-dimensional magnetic resonance imaging dataset. Then, as indicated by the arrows 7, these data subsets can be acquired again in respective reserved sub-periods 3, wherein the previous corresponding magnetic resonance data are discarded.

Figure 2:
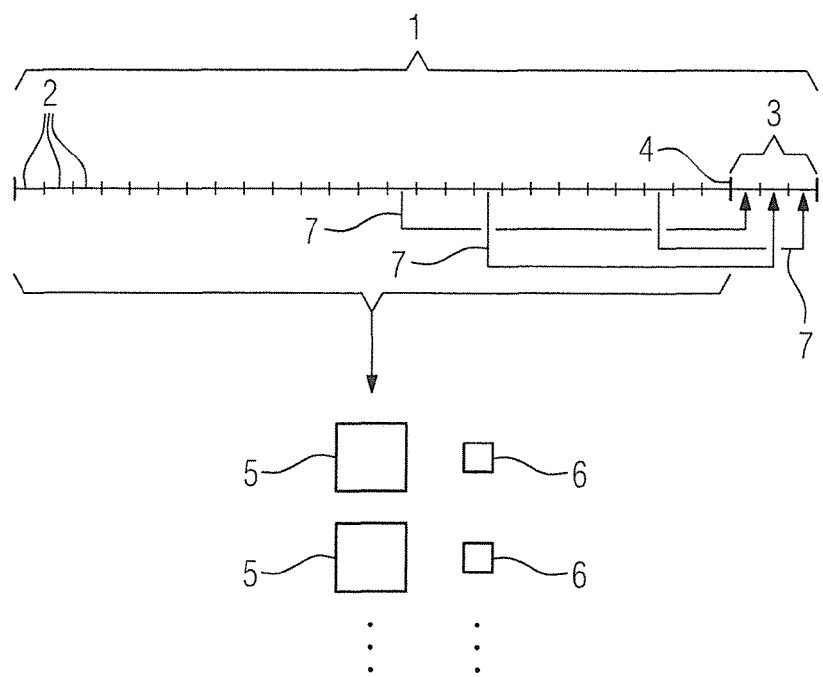
FIG. 2 illustrates data subsets to be acquired again in reserved sub-periods.

At this point, it is noted once again that the schematic sketch in FIG. 2 is only for purposes of explanation. Usually, the duration of an acquisition period can, for example, be in the range of a few minutes, for example in the range of 3 to 10 minutes. In this case, the sub-periods can be selected in the range of seconds, for example in the range of from 1 to 20 seconds, in particular 10 seconds.

In a Step S12, the acquisition of motion data is completed and now the number n of data subsets 5 with assigned motion values 6 is available and these are now used in order to divide the data subsets 5 into different motion status classes, which can be defined with reference to the existing motion values 6 themselves or prespecified over specific intervals for the motion values 6. If all of the at least one motion value 6 of a subclass 5 fall within all of the at least one interval for the motion value 6 assigned to a motion status class, the sub-dataset 5 is evaluated as part of this motion status class. Similarly, it is now decided in Step S12 which magnetic resonance data of which data subsets 5, i.e. specifically of which motion status classes, should contribute to the reconstruction of the three-dimensional magnetic resonance imaging dataset. At the same time, selection criteria are used, wherein, for example, a motion status class can be selected that contains the majority of magnetic resonance data, i.e. the majority of data subsets 5, wherein the quality criteria describing suitability for the reconstruction can also be taken into account for the motion value 6 and/or the magnetic resonance data of the motion status class. For example, it is possible to monitor whether sufficiently uniform coverage of k-space is provided.

This is explained in more detail below with reference to FIGS. 3 and 4. These both show in histograms the number N of data subsets 5 in motion status classes Z, which are here defined by intervals for the motion value 6. According to FIG. 3, one motion status class 8 contains the majority of data subsets 5, i.e. the majority of the magnetic resonance data, so that this motion status class 8 is fundamentally selected in order to reconstruct the three-dimensional magnetic resonance imaging dataset for this motion status. However, this does not exclude the possibility that, during the now subsequent reconstruction, magnetic resonance data of not greatly deviating motion statuses can also be taken into account, wherein, in the present case, in addition to the selected motion status class, magnetic resonance data of the motion status classes 9 and 10 are included in the reconstruction since this satisfies a deviation criterion for the motion values 6, which indicates that the deviation of the motion statuses is only low. However, this magnetic resonance data of the motion status classes 9 and 10 are included in the reconstruction with less weighting, wherein the weighting is selected in dependence on the degree of deviation of the motion status from the reference motion status defined by the motion status class 8 after the acquisition process.

Figure 3:
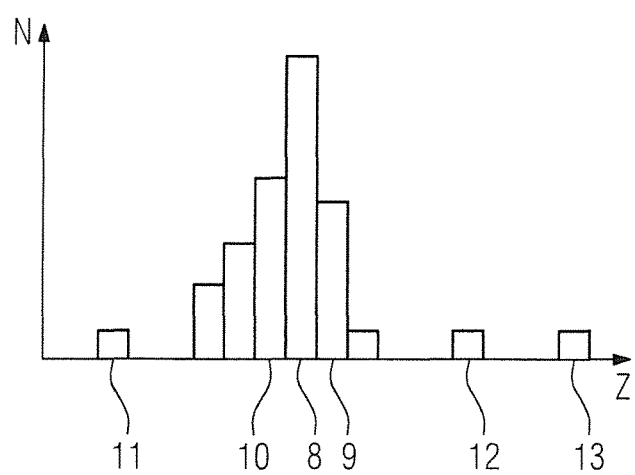
FIG. 3 is a histogram showing the distribution of data subsets among motion status classes in a first exemplary embodiment.

The histogram in FIG. 3 also shows individual data subsets in the motion status classes 11, 12 and 13, the motion statuses of which deviate significantly from the selected motion status class 8 and which represent classical candidates for a repeat measurement in reserved sub-periods 3, as explained with respect to FIG. 2, if the histogram observation shown here is performed after real-time classification of the data subsets 5 in Step S11.

Figure 4:
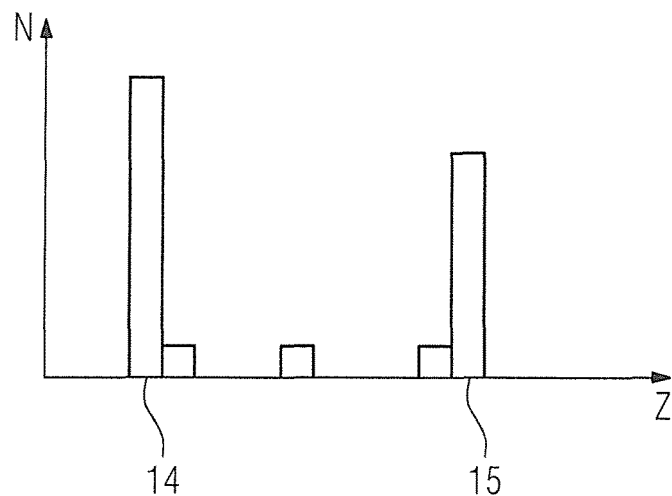
FIG. 4 shows an example of the distribution of data subsets among motion status classes in the case of motion that has taken place and not been reversed during the acquisition process, in a second exemplary embodiment.

FIG. 4 shows a further example of a histogram indicating the number of data subsets in motion status classes Z. In the case shown there, the patient fell asleep during the acquisition process so that an actual motion only took place at a specific time point or in a specific short time interval or otherwise the area to be examined was substantially motionless. This is expressed in the fact that the majority of data subsets are sorted in the motion status class 14, which as the selected motion status class 14 should also be used as the basis for the reconstruction. Nevertheless, there is also a notable number of data subsets 5 in motion status class 15 with a motion status that differs significantly from that of motion status class 14. Nevertheless, the magnetic resonance data of motion status class 13 can be included in the reconstruction when correction is possible, which, in the present case, is covered in Step S12 by a correctability criterion. To this end, a comparative measure, in this case a mutual information measure, is formed in the position-space, which ultimately shows suitability for registration of the magnetic resonance data, specifically from their reconstructed intermediate image datasets, with respect to one other. If the correctability criterion is satisfied, the corresponding registration is determined and the magnetic resonance data of the motion status class 13 is converted to the motion status of motion status class 14 by a corresponding motion correction and can be included in the reconstruction. During the determination of this registration, which is definitely justified due to the large amount of magnetic resonance data in both motion status classes 13, 14, the motion values 6 or their underlying motion data describing the motion, are taken into account for the modeling of the motion by motion parameters and/or at least for setting boundaries for registration parameters.

A combination of these two variants is also possible for the determination of further motion status classes 9, 10, 13 to be taken into consideration for the purposes of the reconstruction in order to obtain the broadest possible basis for the reconstruction of the three-dimensional image dataset.

If all magnetic resonance data or data subsets 5 to be included in the reconstruction have been identified, the reconstruction is performed in Step S13, once again see FIG. 1. At the same time, expediently with incoherent sampling, an iterative reconstruction method is used, while, with coherent sampling of k-space, a linear reconstruction method, in particular a GRAPPA method, is used.

Figure 5:
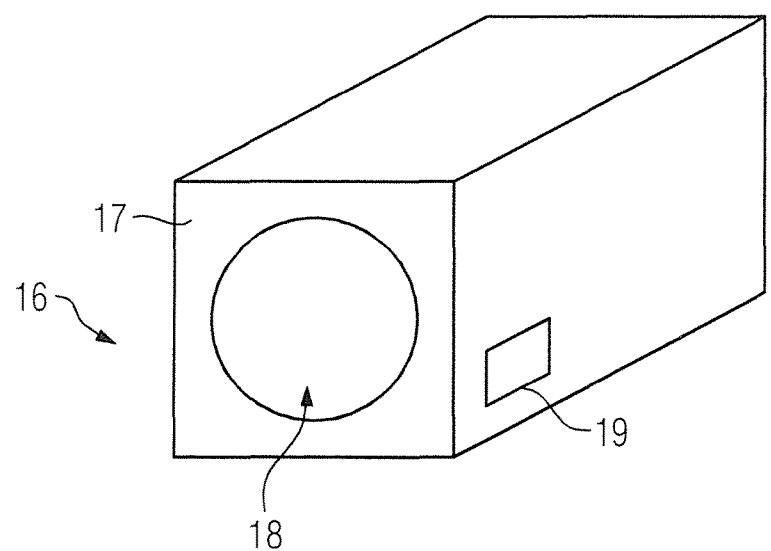
FIG. 5 schematically illustrates a magnetic resonance apparatus according to the invention.

Finally, FIG. 5 shows a schematic sketch of a magnetic resonance apparatus 16 according to the invention. As is in principle known, this has a scanner 17 with a basic field magnet that defines a patient receiving area 18 in which a patient can be introduced by a patient bed (not shown). Here, the patient receiving area 18 is generally also surrounded by a gradient coil arrangement and a radio-frequency coil arrangement.

The operation of the scanner 17 of the magnetic resonance apparatus 16 is controlled by a control computer 19 designed for the performance of the method according to the invention. To this end, the control computer 19 has at least one acquisition stage or module or processor that for controlling the further components of the magnetic resonance scanner 17 for acquiring magnetic resonance data the data subsets, a motion monitoring stage or module or processor that for the determination of the motion values 6, and a reconstruction computer, which also takes over the selection of the data subsets included in the reconstruction. A further stage or module or processor that can be an analysis unit able to carry out the described histogram observations and also the division into motion status classes.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for acquiring a magnetic resonance imaging data set of an examination region of a patient, comprising:
providing a control computer with a predetermined uninterrupted acquisition period for a data acquisition procedure for operating a magnetic resonance data acquisition scanner, in order to continuously acquire magnetic resonance raw data from an examination region of a patient and, in said control computer, dividing said uninterrupted acquisition period into a plurality of sub-periods;
using said control computer to operate said scanner to execute said data acquisition procedure so as to continuously acquire said raw magnetic resonance data from the examination region in each of said sub-periods individually, and entering the acquired raw data for each sub-period into an electronic memory representing k-space, thereby obtaining a plurality of data subsets in k-space respectively for the sub-periods, with each data subset being undersampled in k-space;

for each sub-period, determining a motion value that represents a motion status, during the respective sub-period, of said examination region;

in an image reconstruction computer, executing an image reconstruction algorithm to reconstruct an image of the examination region from said magnetic resonance raw data in k-space and, in said reconstruction algorithm, selecting data subsets from said electronic memory, based on said motion value of each sub-period, according to a selection criterion that minimizes motion artifacts in said image, and using only the selected data subsets in said reconstruction algorithm to reconstruct said image; and making the reconstructed image of the examination region available in electronic form from said reconstruction computer as a data file.

2. A method as claimed in claim 1 comprising operating said scanner to acquire said magnetic resonance raw data from said examination region in each of said sub-periods as three-dimensional magnetic resonance raw data.

3. A method as claimed in claim 1 comprising dividing said uninterrupted predetermined acquisition period into a plurality of equally long sub-periods.

4. A method as claimed in claim 1 comprising determining said motion value for each data subset from the respective data subset itself.

5. A method as claimed in claim 4 comprising, in each sub-period, acquiring a magnetic resonance navigator and thereby including navigator data in each data subset in k-space, and determining the motion value for each data subset from the navigator data thereof.

6. A method as claimed in claim 4 comprising, from each individual data subset, determining a quality measure from the k-space data thereof and using said quality measure as said motion value for that respective data subset.

7. A method as claimed in claim 1 comprising determining the motion value for each data subset by implementing a measurement that is separate from the acquisition of the magnetic resonance raw data for that respective data subset.

8. A method as claimed in claim 7 comprising implementing said separate measurement as a measurement from the group consisting of using a camera to track a camera-detectable marker on the patient, obtaining an electronic signal representing respiratory movement from a breathing belt worn by the patient, and using a field camera to detect patient movement-induced changes in a magnetic field in said scanner.

9. A method as claimed in claim 1 comprising, for each sub-period, entering the magnetic resonance raw data acquired during that respective sub-period into k-space according to a data entry technique selected from the group consisting of stochastic data entry, pseudo-random data entry, and data entry according to a regular pattern.

10. A method as claimed in claim 1 comprising, for each sub-period, entering the magnetic resonance raw data thereof into k-space according to an incoherent sampling technique, and reconstructing said image of said examination region with an iterative reconstruction algorithm as said reconstruction algorithm.

11. A method as claimed in claim 1 comprising, for each sub-period, entering the raw magnetic resonance data thereof into k-space according to a coherent sampling technique, and reconstructing said image of said examination region with a linear reconstruction algorithm, as said reconstruction algorithm.

12. A method as claimed in claim 1 comprising using said criterion that minimizes motion artifacts in said reconstructed image to sort said data subsets in k-space into at least two motion status classes dependent on the respective motion values thereof.

13. A method as claimed in claim 12 wherein said sorting of said data subsets into at least two motion status classes produces a motion status class in which a majority of said magnetic resonance raw data are present, and using only the data subsets in said motion status class having said majority of said magnetic resonance raw data in said reconstruction algorithm.

14. A method as claimed in claim 12 comprising sorting said data subsets into said at least two motion status classes dependent on a quality criterion for said motion value, and selecting said data subsets for reconstructing said image in said reconstruction algorithm only from motion status classes that satisfy said quality criterion.

15. A method as claimed in claim 12 comprising selecting data subsets for use in reconstructing said image in said reconstruction algorithm from a motion status class, among said at least two motion status classes, dependent on said criterion that minimizes motion artifacts in said image, and from at least one motion status class, among said at least two motion status classes, that is within a predetermined permissible deviation from said criterion that minimizes motion artifacts in said image.

16. A method as claimed in claim 15 comprising, in said reconstruction algorithm, weighting magnetic resonance raw data in data subsets in said motion class that satisfies said criterion for reducing motion artifacts in said image more heavily than magnetic resonance raw data in data subsets in said motion status class having said predetermined permissible deviation from said motion criterion that minimizes motion artifacts in said image.

17. A method as claimed in claim 12 comprising selecting data subsets for use in reconstructing said image in said reconstruction algorithm from a motion status class, among said at least two motion status classes, dependent on said criterion that minimizes motion artifacts in said image, and from at least one motion status class, among said at least two motion status classes, that satisfies a correctability criterion representing a degree to which an effect of motion on the magnetic resonance raw data can be corrected.

18. A method as claimed in claim 17 comprising using, as said correctability criterion, a measure representing a degree to which a registration of a first intermediate image data set, derived from magnetic resonance raw data in data subsets in said motion status class that satisfies said criterion for reducing motion artifacts in said image, can be brought into registration, with a registration deviation that does not exceed a predetermined threshold, with a second intermediate image data set derived from magnetic resonance raw data in data subsets in said motion status class that satisfies said correctability criterion.

19. A method as claimed in claim 17 comprising, in said reconstruction algorithm, performing a motion correction at least on magnetic resonance raw data in the data subsets in the motion status class that satisfies said correctability criterion, by modeling based on a motion parameter derived from said motion value, or by restricting use of the magnetic resonance raw data in said data subsets in said motion status class that satisfies said correctability criterion.

20. A method as claimed in claim 1 comprising, at an end of said uninterrupted acquisition period, reserving at least one reserved sub-period and, in said reserved sub-period, repeating acquisition of raw magnetic resonance data from one of said sub-periods that is dynamically selected dependent on an evaluation of all motion values of all of the sub-data sets for which magnetic resonance raw data were acquired before said reserved sub-period.

21. A method as claimed in claim 19 comprising reserving a plurality of sub-periods, and selecting said plurality dependent on patient information that predicts motion of said patient.

22. A method as claimed in claim 21 comprising obtaining said patient information from at least one source selected from the group consisting of magnetic resonance data acquired from the patient in a data acquisition in said scanner that precedes said data acquisition procedure, and patient behavior characteristics that are manually entered into said control computer.

23. A method as claimed in claim 1 wherein k-space comprises a k-space area that corresponds to said examination region, and wherein each of said data subsets encompasses a different component of said k-space area.

24. A method as claimed in claim 23 wherein said k-space area comprises a center of k-space and, in at least two of said sub-periods, entering the magnetic resonance raw data in the respective data subsets thereof with a predetermined region around said k-space center being completely sampled or sampled with a predetermined undersampling factor.

25. A method as claimed in claim 1 comprising operating said scanner with said magnetic resonance data acquisition procedure at an end of an overall examination of the patient in the scanner, and determining said predetermined acquisition period as a remainder of a total time of said total examination minus a time of said total examination that precedes said magnetic resonance data acquisition procedure.

26. A method as claimed in claim 1 comprising selecting said data subsets for use in said reconstruction algorithm during said acquisition procedure by, for a currently-acquired data subset, reconstructing a preliminary image of the examination region from a preceding data subset that precedes the currently-acquired data subset and, when the image reconstructed from said preceding data subset satisfies a quality criterion representing a minimum image quality requirement, aborting said acquisition procedure before completion thereof.

27. A method as claimed in claim 20 comprising reconstructing said image of said examination region from said preceding data subset as a two-dimensional slice image of the examination region.

28. A method as claimed in claim 1 comprising, during said acquisition procedure, comparing each of said motion values, as said data subsets are acquired, to a motion criterion and, upon an occurrence of any motion value that exceeds said motion criterion, automatically emitting, via said control computer, a humanly perceptible alert that indicates excessive motion of the patient.

29. A magnetic resonance apparatus comprising:
a magnetic resonance data acquisition scanner adapted to receive a patient therein;
a control computer provided with a predetermined uninterrupted acquisition period for a data acquisition procedure in order to continuously acquire magnetic resonance raw data from an examination region of a patient and, in said control computer being configured to divide said uninterrupted acquisition period into a plurality of sub-periods;
an electronic memory;
said control computer being configured to operate said scanner to execute said data acquisition procedure to acquire raw magnetic resonance data from the examination region in each of said sub-periods individually, and to enter the acquired raw data for each sub-period into said electronic memory as k-space data in k-space, thereby obtaining a plurality of data subsets in k-space respectively for the sub-periods, with each data subset being undersampled in k-space;
said control computer being configured to determine, for each sub-period, a motion value that represents a motion status, during the respective sub-period, of said examination region;
an image reconstruction computer configured to execute an image reconstruction algorithm to reconstruct an image of the examination region from said magnetic resonance raw data in k-space and, in said reconstruction algorithm, to select data subsets from said electronic memory, based on said motion value of each sub-period, according to a selection criterion that minimizes motion artifacts in said image, and to use only the selected data subsets in said reconstruction algorithm to reconstruct said image; and
said reconstruction computer being configured to make the reconstructed image of the examination region available in electronic form from said reconstruction computer as a data file.

* * * * *